United States Patent [19]

Tucker

[11] 4,413,620

[45] Nov. 8, 1983

[54] ABDOMINAL RESTRAINT SYSTEM

[75] Inventor: Samuel M. Tucker, Barrington, Ill.

[73] Assignee: The Kendall Company, Walpole, Mass.

[21] Appl. No.: 304,519

[22] Filed: Sep. 21, 1981

[51] Int. Cl.³ .............................................. A61F 5/37
[52] U.S. Cl. ................................... 128/134; 128/385; 128/721; 128/24 R
[58] Field of Search ............................... 128/133–134, 128/327, 677, 680, 682, 683, 721–723, 716, 384–385, 782, 24 R

[56] References Cited

U.S. PATENT DOCUMENTS

| | | | |
|---|---|---|---|
| 2,899,955 | 8/1959 | Huxley et al. | 128/30 |
| 3,278,185 | 10/1966 | Bidopia et al. | 272/139 |
| 3,454,000 | 7/1969 | Bird et al. | 128/28 |
| 3,481,327 | 12/1967 | Drennen | 128/30.2 |
| 3,683,655 | 8/1972 | White et al. | 128/30.2 |
| 3,976,056 | 8/1976 | Brawn | 128/24 R |
| 4,077,402 | 3/1978 | Benjamin, Jr. et al. | 128/24 R |

OTHER PUBLICATIONS

Barlow, "Cough–Belt to Prevent and Treat Postoperative Pulmonary Complications," *Lancet*, 10/64, p. 736.

*Primary Examiner*—Lee S. Cohen
*Assistant Examiner*—Angela D. Sykes
*Attorney, Agent, or Firm*—James W. Potthast

[57] ABSTRACT

An abdominal restraint system for protecting a patient from the strain of a cough or the like in which an abdominal belt is tightened around the patient in response to physiological conditions of the patient associated with onset of a cough or the like. Detection of cough onset is achieved by means of pressure sensors, body movement sensors or both. Controlled restraint is achieved by selective inflation or mechanical tightening of the belt.

21 Claims, 1 Drawing Figure

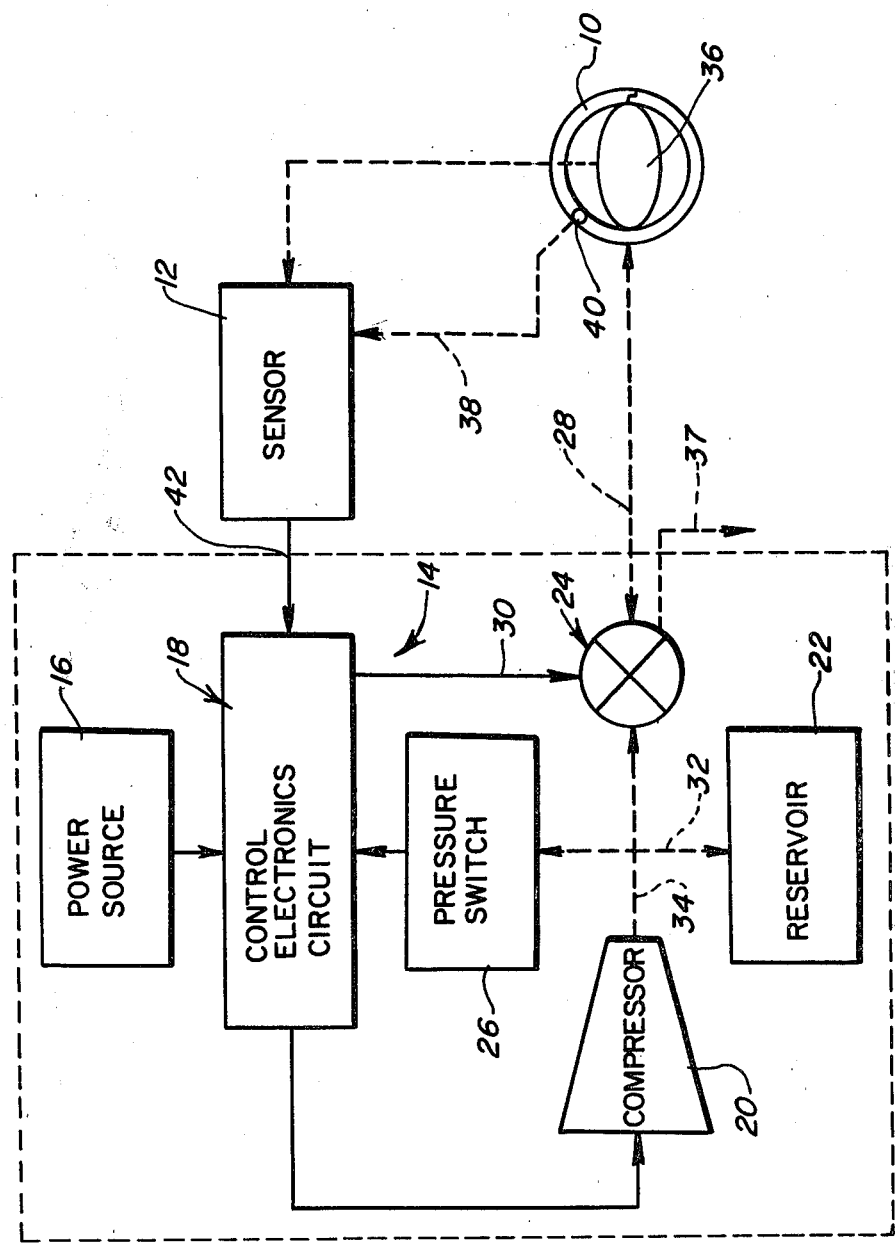

ABDOMINAL RESTRAINT SYSTEM

BACKGROUND OF THE INVENTION

1. Field of the Invention

This invention relates to a system for providing restraint to the abdominal area of a patient in response to physiological conditions associated with onset of a cough or the like.

2. Description of the Prior Art

The strain of coughing, sneezing or the like can have deleterious and painful effects on the patient suffering from injuries or illness in the trunk area of the patient's body, particularly the abdominal area. For instance, for a patient recovering from abdominal surgery, the strain of a cough or sneeze can often break or loosen the sutures. As set forth in an article by Donald Barlow, entitled "A Cough-Belt to Prevent and Treat Post-Operative Pulmonary Complication" and appearing at page 736 of the Oct. 3, 1964 issue of the Lancet, other patients who suffer from the strain of coughing and the like include those with fractured ribs or other chest ailments.

In this article, Barlow has recommended a "cough-belt" to alleviate this problem. The cough-belt is to be worn by the patient around his abdominal area to restrain excessive body movement in the abdominal or chest area during a cough or the like. This belt is manually adjustable to fit patients of different abdominal size, but no means are provided for automatic adjustment immediately prior to or during the cough. Accordingly, the degree of restraint during the cough can be no greater than that which is tolerable to the patient during non-coughing. Nontheless, in order to achieve the requisite amount of restraint during a cough, it may be necessary to make the belt tighter around the patient during the non-coughing periods than is comfortable for the patient. On the other hand, in order to make the belt comfortable to the patient during non-coughing periods, it may be required to have the belt looser than would be optimally desired during a cough.

While no solution is proposed for this problem, patents are known in which automatic adjustments to a belt-like device on a patient may be made. In U.S. Pat. No. 4,077,402 of Benjamin, the pressure of an inflatable cuff for promoting blood circulation is controlled in accordance with sensed heartbeat and blood flow. In U.S. Pat. No. 3,683,655 of White et al, a respiratory belt is shown in which the inflation (exhalation) cycle is initiated by means of an electronic controller. The controller pressurizes the belt in response to the patient's exhalation sensed by a microphone in the path of his oral or nasal passageway. In U.S. Pat. No. 3,976,056 of Brawn, a pressure stocking for a leg is pressurized by body movements which compress a primary air sac attached to the patient's body. The air is forced out of the primary air sac by means of small diameter tubes or valves.

Other references disclose inflatable belts in which the inflation of the belt is rythmically varied to assist the patient's breathing. See, for instance, U.S. Pat. Nos. 2,899,955 of Huxley III et al; 3,454,000 to Bird et al; and 3,481,327 to Drennen.

Reference may also be had to U.S. Pat. No. 3,278,185 of Bidopia for an example of a mechanically adjustable belt. An exercise belt is provided with a spring agaist which the wearer exercises his abdominal muscles.

SUMMARY OF THE INVENTION

In accordance with the principal object of my invention, the aforementioned problems of the prior art are overcome by providing an abdominal restraint system in which the degree or amount of restraint provided by the system is increased during a cough relative to the degree of restraint provided during non-coughing periods, so that both optimal protection and optimal comfort are obtained.

In keeping with this objective, in a preferred embodiment, I provide an abdominal restraint system having means for providing a controlled amount of restraint against movement to a part of the trunk of the patient's body, means connected with the patient for detecting the onset of a cough or the like by the patient; and means responsive to the detecting means for controlling the restraint providing means to increase the amount of the restraint during the cough or the like.

An inflatable or otherwise adjustable abdominal belt provides the controlled amount of restraint. If inflatable, the degree of restraint is increased by inflating the belt. If a non-inflatable belt is employed, the restraint is increased by tightening the belt.

Although other means may work suitably, preferably the onset of a cough is detected by sensing pressure changes in parts of the patient's body, particularly the stomach, esophagus and laryngeal/pharyngeal area, or body movements uniquely associated with onset of a cough or the like. When the onset of a cough is detected, a controller is actuated to increase the degree of restraint provided by the abdominal belt. In the case of an inflatable belt, this is achieved by opening a valve interconnecting a source of pressure with the belt to increase the belt pressure. After the cough has subsided, the pressure is released to reduce the restraint to a more comfortable level.

DESCRIPTION OF THE DRAWING

The foregoing objects and features of my invention will be made more apparent, and further features, objects and advantages will be disclosed in the following detailed description which is given with reference to the block diagram of a preferred embodiment of my abdominal restraint system.

DETAILED DESCRIPTION

Referring now to the drawing, my abdominal restraint system is seen to include, in principal parts, a controlled restraint providing means 10, cough onset detecting means, or sensors, 12 and a restraint controller 14. The restraint controller comprises a source of electrical power, or power source, 16, a control electronics circuit 18, an air compressor 20, a pressure tank, or reservoir, 22, a solenoid controlled valve 24, and a pressure switch, or pressure transducer, 26.

As indicated by broken line 28, the belt 10 has a mechanical linkage with the restraint controller 14. In the event of belt 10 being an inflatable belt, as illustrated in the drawing, then the mechanical linkage simply comprises a tubular passageway, or conduit, 28 between the interior portion of the belt 10 and valve 24. The valve 24 is actuated by energization of a solenoid or the like (not shown) from an electrical output 30 of the control electronics circuit 18. When the control electronics circuit 18 energizes the solenoid, the valve 24 is caused to open. This permits the pressurized air to flow from reservoir 22 and from compressor 20 and valve inlet 34 through valve 24 and conduit 28 into restraint belt 10 to cause it to tighten about the abdomen of patient 36.

When not energized, the valve 24 remains in a closed position in which pressurized air from reservoir 22 is blocked from entering belt 10. However, the pressurized air in belt 10 is permitted to flow through conduit 28 and escape to atmosphere through a leakage port 37 of solenoid valve 24. This causes the belt 10 to gradually deflate after the cough has subsided and thereby decrease the restraint on the patient's abdomen to a level of greater comfort. Alternately, the belt 10, itself, can be provided with built in leakage to insure return of the belt to a deflated condition after the cough, sneeze or the like.

In the unenergized position, the pressurized air in the reservoir 22 is maintained at a selected pressure level by means of pressure switch 26 and control electronics circuit 18. When the pressure drops below a desired level associated with the pressure switch, the pressure switch 26 is actuated. This causes the control electronics circuit 18 to energize the compressor to increase the pressure in the reservoir. The pressure switch 26 also may provide a safety feature and cause the control electronic circuit 18 to keep solenoid controlled valve 24 in a closed position and to terminate power to compressor 20 from power source 16 in the event of an excessively high pressure condition.

If a non-inflatable belt 10 is employed, then the mechanical linkage 28 comprises a mechanical power train for tightening the belt by moving one end of the belt away from the other end around the loop formed by the belt.

The sensors 12 comprise any one of a variety of suitable pressure sensors which are used in association with one or more catheters inserted into the patient to directly monitor pressure changes at selected parts of the patient's body. Alternately, as depicted by the broken line arrow 38 interconnecting the belt 10 and the sensors logic block 12, the sensors 12 may comprise body movement sensors 40 mounted within the belt or elsewhere for detecting particular body movements of the patient uniquely associated with the onset of a cough, sneeze or the like. Also alternately, both types of sensors 12 may be used together.

The pressure change or body movement of the patient is detected by sensors 12 and converted to corresponding electrical signals which are applied from the output 42 of the sensors block 12 to an output of control electronic circuit 18. Conventional control electronics circuit 18 functions to determine if a particular combination of pressures or body movements or both is indicative of the onset of a cough. If the signals indicate that the patient is about to cough or sneeze, than the control electronics circuit 18 generates an actuation signal on its output 30 to quickly tighten belt 10 to increase the abdominal restraint on patient 36. The control electronics circuit 18 automatically terminates energization and permits loosening of the belt 10 after a preselected time or in response to another combination of sensor signals indicative of the termination of a cough or of a non-coughing period. It is believed that such unique pressure changes associated with onset of a cough are most readily ascertainable and detectable in the stomach, esophagus and laryngeal/pharyngeal areas. For instance, the cough will have a particular part of the chest where compression or rarifaction will occur first before other pressure changes or body movements associated with a cough. The control electronics circuit will only accept those signals as a valid cough onset signal if this particular pressure occurs first.

It should be appreciated that many variations of my preferred embodiment may be made without varying from the scope of my invention. For instance, although a pneumatic system is disclosed and shown in the drawing, it should be understood that a variety of well known mechanical tightening systems could be employed in lieu of such an inflation system. Further, although I prefer to rely upon the pressure sensors and mechanical movement sensors for data acquisition relevant to cough onset, there are probably other physiological changes associated with onset of a cough which could also be used for cough detection purposes. Furthermore, although I intend my invention to be principally used in connection with coughs and sneezes, it clearly could also be employed to provide additional abdominal restraint in response to conditions indicative of the onset of a laugh, hiccups, etc.

I claim:
1. An abdominal restraint system, comprising:
   means for providing a controlled amount of restraint against movement to a part of the trunk of a patient's body;
   means for connection with the patient to detect the onset of a cough or the like by the patient; and
   means responsive to said detecting means for controlling the restraint providing means to increase the amount of restraint during the cough or the like.
2. The abdominal restraint system of claim 1 in which the restraint providing means comprises a belt and said controlling means comprises means for tightening the belt.
3. The abdominal restraint system of claim 2 in which
   said belt is inflatable to increase restraint, and
   said controlling means includes means for inflating the belt.
4. The abdominal restraint system of claim 3 in which said belt is of a size to fit around the patient's abdomen.
5. The abdominal restraint system of claim 1 in which said detecting means includes means for sensing a pressure change in a part of the patient's body.
6. The abdominal restraint system of claim 1 in which said detecting means includes means for detecting pressure changes in a plurality of parts of a patient's body.
7. The abdominal restraint system of claim 6 in which said detecting means includes means for detecting an onset of a cough only in response to a preselected sequence of pressure changes.
8. The abdominal restraint system of claim 7 in which said plurality of parts includes at least one of the patient's stomach, esophagus and laryngeal/pharyngeal areas.
9. The abdominal restraint system of claim 1 in which said detecting means detects the onset of a cough only in response to a pre-selected combination of pressure changes in the patient's body.
10. The abdominal restraint system of claim 1 in which said detecting means includes a pressure sensor connected with a catheter insertable into the patient for sensing the pressure changes in a part of the patient's body.
11. The abdominal restraint system of claim 10 in which a plurality of pressure sensors are mounted in the catheter to detect a plurality of pressures in the patient's body.
12. The abdominal restraint system of claim 1 in which said detecting means includes means for sensing preselected body movements associated with onset of a cough.

13. The abdominal restraint system of claim 12 in which
the restraint providing means comprises a belt for positioning around the patient's body, and
said body movement sensing means are mounted to said belt.

14. The abdominal restraint system of claim 13 in which said detecting means includes a pressure sensor associated with a patient catheter for directly sensing the pressure in a patient's body.

15. The abdominal restraint system of claim 14 in which said detecting means detects the onset of a cough only in response to signals from both said pressure sensor and said body movement sensing means.

16. The abdominal restraint system of claim 1 in which said controlling means includes
a source of pressure,
a valve connected with said source of pressure, and
means for selectively operating said valve in response to said detecting means.

17. A method of protecting a patient's body from the strain of a cough or the like, comprising the steps of:
detecting the onset of a cough; and
providing increased restraint to the patient during the cough in response to said detection.

18. The method of claim 17 in which said step of detecting includes the step of monitoring the pressure change of a part of the patient's body, said pressure change being associated with onset of a cough or the like.

19. The method of claim 17 in which said step of detecting includes the step of monitoring selected movement of a patient's body, said selected movement being associated with the onset of a cough.

20. The method of claim 17 in which said step of providing restraint includes the step of tightening a belt about the patient's abdominal area.

21. The method of claim 20 in which said step of tightening includes the step of inflating said belt.

* * * * *